United States Patent [19]  [11]  4,404,218
Ito et al.  [45]  Sep. 13, 1983

[54] ANTIBIOTIC SF-2103A SUBSTANCE AND PROCESS FOR PRODUCTION THEREOF

[75] Inventors: Tatsuo Ito, Isehara; Takashi Shomura, Yokohama; Michio Kojima, Tokyo; Norio Ezaki, Yokohama; Masaji Sezaki, Tokyo; Tomizo Niwa, Yokohama, all of Japan

[73] Assignee: Meiji Seika Kaisha Ltd., Tokyo, Japan

[21] Appl. No.: 293,063

[22] Filed: Aug. 17, 1981

[30] Foreign Application Priority Data

Aug. 19, 1980 [JP] Japan ................................ 55-112996
Nov. 11, 1980 [JP] Japan ................................ 55-157631

[51] Int. Cl.³ .................... C07D 487/04; A61K 31/40
[52] U.S. Cl. ............................ 424/274; 260/245.2 T; 424/114; 435/119
[58] Field of Search .................. 260/245.2 T; 424/274

[56] References Cited

FOREIGN PATENT DOCUMENTS 55-157631 11/1980 Japan .

OTHER PUBLICATIONS

International Journal of Systematic Bacteriology, vol. 18, pp. 69–189, Apr. 1968.

Primary Examiner—Mary C. Lee
Attorney, Agent, or Firm—Sughrue, Mion, Zinn, Macpeak & Seas

[57] ABSTRACT

An antibiotic SF-2103A substance or a salt thereof, and a process for the production thereof are described, and the process comprises cultivating an antibiotic SF-2103A substance-producing strain in a nutrient medium and recovering the desired substance from the culture broth.

3 Claims, 3 Drawing Figures

ANTIBIOTIC SF-2103A SUBSTANCE AND PROCESS FOR PRODUCTION THEREOF

FIELD OF THE INVENTION

The present invention relates to a novel antibiotic SF-2103A substance and salts thereof, and a process for the production thereof.

BACKGROUND OF THE INVENTION

It has been known that various microorganisms can produce antibiotic substances upon cultivation in a nutrient medium containing assimilable carbon and nitrogen sources. However, a continuing need exists for new and useful antibiotic substances.

SUMMARY OF THE INVENTION

As a result of extensive studies to find novel and useful antibiotics having antibacterial activity against various gram-positive and gram-negative bacteria, including bacteria which are resistant to known antibiotics, it has been discovered that a novel antibiotic, herein designated as an SF-2103A substance, can be obtained by cultivating a strain belonging to the genus Streptomyces in a nutrient medium.

The antibiotic SF-2103A substance has been isolated, and the physical and chemical properties, and biochemical characteristics thereof, have been confirmed.

The present invention, therefore, provides a novel antibiotic SF-2103A substance represented by the formula

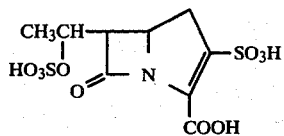

and salts thereof, and a process for the production of the antibiotic SF-2103A substance and salts thereof.

DETAILED DESCRIPTION OF THE INVENTION

Figure 1:
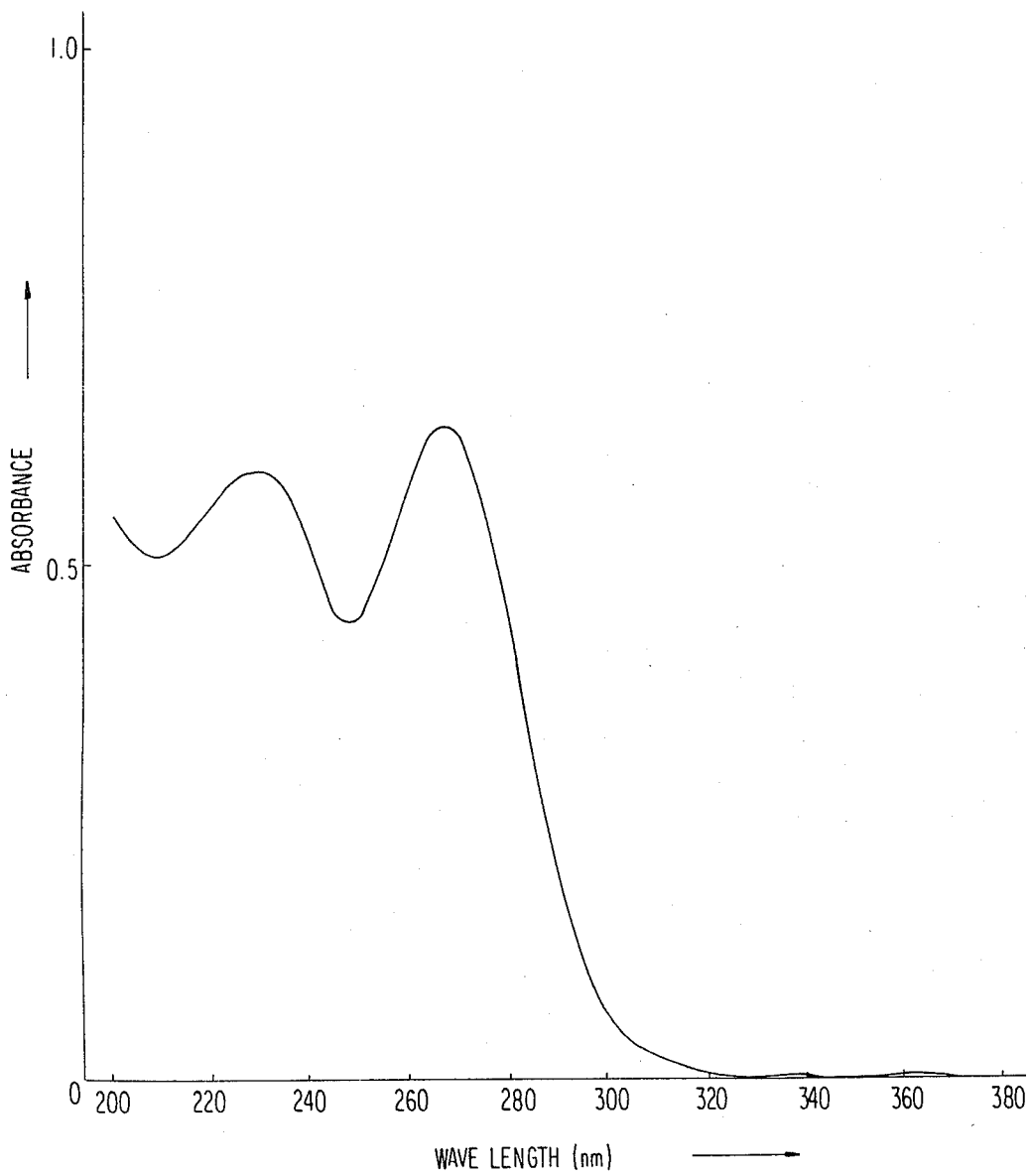
FIGS. 1, 2 and 3 are an ultraviolet absorption spectrum, an infrared absorption spectrum, and a nuclear magnetic resonance spectrum, respectively, of the antibiotic SF-2103A substance (sodium salt).

An example of antibiotic SF-2103A substance-producing strains as used herein is Actinomyces SF-2103 strain isolated from a soil collected from Katsuura, Wakayama Prefecture, Japan.

Four grams of the soil were suspended in 40 ml of sterilized water in a 100-ml Erlenmeyer flask, stirred on a rotary shaker for 10 minutes, which was then allowed to stand for 15 minutes. At the end of that time, 4 ml of the supernatant was diluted 10,000-fold with sterilized water. Then, 0.5 ml of the thus-diluted liquid was placed on a Petri dish, sterilized in advance, fully mixed with 20 ml of an agar medium for separation as described hereinafter, maintained at 45° to 50° C., and then solidified.

The Petri dish was cultured at 28° C. for 10 days, and colonies of the SF-2103 strain growing on the agar medium were transferred to a yeast-starch agar slant (yeast extract: 0.2%; soluble starch: 1.0%; agar: 2.0%; pH: 7.0).

The composition of the agar medium for separation was as follows: yeast extract: 0.05%; soluble starch: 0.25%; agar: 2.0%; remainder: tap water; pH 7.0.

The characteristics of the Actinomyces SF-2103 strain are as follows:

(I) Morphological Characteristics

Acerial mycelium and spores are formed in culture media such as starch agar, oatmeal agar, and yeast-malt agar. The branching of aerial mycelium is monopodial and whirl-like branching is not found. At the top end of the aerial mycelium, spores are chained almost straight. No special structures such as sclerotium and sporangium are observed.

Microscopic observation shows that spores having a smooth surface, an oval or egg-like form, and a size of 0.7 to 0.8×1.0 to 1.5 microns, and generally form a chain of 10 or more spores.

(II) Culture Characteristics

The culture characteristics of the SF-2103 strain on various culture media are shown in Table 1 below. The observation was carried out after cultivation at 28° C. for 14 to 21 days. The color shown in Table 1 was identified according to the color standard of the Color Harmony Manual, 4th Edition, published by Container Corporation of America, Chicago, Ill. (1958).

The pale pink color of the aerial mycelium on starch agar, oatmeal agar and yeast-malt agar media readily disappears with decreasing spore-forming ability. Furthermore, the aerial mycelium shows a strong tendency to melt and disappear as the cultivation proceeds over a certain period of time.

TABLE 1

| Culture Medium | Growth and Reverse Color | Aerial Mycellium | Soluble Pigment |
|---|---|---|---|
| Sucrose-nitrate agar | Very scant growth colorless | None | None |
| Glucose-asparagine agar | Scant growth, colorless | None | None |
| Glycerol-asparagine agar | Scant growth, colorless | None | None |
| Starch agar | Moderate growth, pale beige | Moderate, pale pink (5cb) | Slight grey-pink |
| Oatmeal agar | Moderate growth, pale beige | Moderate, pale pink (5cb) | None |
| Yeast-malt agar | Good growth, pale beige | Moderate, pale pink (5cb) | None |
| Tyrosine agar | Scant growth, colorless | None | None |
| Nutrient agar | Scant growth, | None | None |

TABLE 1-continued

| Culture Medium | Growth and Reverse Color | Aerial Mycellium | Soluble Pigment |
| --- | --- | --- | --- |
| Calcium malate agar | Scant growth, colorless | None | None |
| Bennett's agar | Good growth, wrinkled | None | None |

(III) Physiological Characteristics (1) Growth Temperature Range: Growth occurs on starch agar at a range of from 15° C. to 42° C., and optimal temperature ranges from 25° C. to 35° C.
(2) Liquefaction of Gelatin: Positive
(3) Hydrolysis of Starch: Positive
(4) Coagulation of Skim Milk: Negative Peptonization of Skim Milk: Positive
(5) Reduction of Nitrate: Negative
(6) NaCl Tolerance: Growth occurs on a culture medium with 3% NaCl added, but not with 5% NaCl added.
(7) Production of Melanoid Pigment: Negative (IV) Utilization of Carbon Sources (Pridham & Gottlieb Agar Medium at 28° C.)

(1) Utilizable: D-Glucose, L-Rhamnose, D-Fructose, D-Xylose, L-Arabinose, D-Mannitol, Sucrose
(2) Not Utilizable: Raffinose, I-Inositol (V) Composition of Cell Wall Analysis according to the method proposed by Becker et al., in *Applied Microbiology*, Vol. 13, p. 236 (1965) shows that diaminopimelic acid contained in the cell wall composition is of LL type.

Summarizing the above-described characteristics, the SF-2103 strain belongs to the genus Streptomyces, and the top end of aerial mycelium is straight, and the surface structure of spores is smooth.

The color tone of matured aerial mycelium belongs to the Red color-series of H. D. Tresner and E. J. Backus, *Applied Microbiology*, Vol. 11, p. 335 (1963), and the reverse color is pale beige. The formation of melanoid pigment is not observed.

Comparing the foregoing taxonomic characteristics of the SF-2103 strain with those of the known strains belonging to the genus Streptomyces, the novel species of SF-2103 strain was identified.

It was found that although there was no known strain which was identical in properties to the SF-2103 strain, *Streptomyces alborubidus* (*International Journal of Systematic Bacteriology*, Vol. 22, pp. 271–273 (1972)) was somewhat similar thereto.

Thus, the standard strain of *Streptomyces alborubidus*, ISP No. 5464 [ISP: International Streptomyces Project (*International Journal of Systematic Bacteriology*, Vol. 18, p. 69 (1968))], and the SF-2103 strain were compared.

They were clearly different from each other with respect to growth on various agar, although they were relatively similar with respect to the color tone of aerial mycelium and the utilization of sugar. That is, the growth of *Streptomyces alborubidus* on sucrose nitrate agar and glucose asparagine agar media was good, and the formation of aerial mycelium was good, whereas the growth of the SF-2103 strain on the foregoing media was very scant, and no formation of aerial mycelium was observed. On the contrary, on an oatmeal agar medium, the SF-2103 strain grew well and the formation of aerial mycelium occurred, whereas the growth of *Streptomyces alborubidus* was scant. Furthermore, the top end of aerial mycelium of *Streptomyces alborubidus* was often observed to be in a loop or hook form, whereas that of the SF-2103 strain was always straight. Moreover, there was no known strain which showed the color tone of aerial mycelium, the Red color-series, the straight aerial mycelium form, and the smooth spore surface which were found to occur for the SF-2103 strain.

Thus, it has been concluded that the SF-2103 strain is different from any species belonging to the genus Streptomyces which have heretofore been reported, and is novel, and the SF-2103 strain has been named *Streptomyces sulfonofaciens* sp. nov.

This strain has been deposited as Streptomyces sp. SF-2103 in the Fermentation Research Institute, Agency of Industrial Science and Technology, Ministry of International Trade and Industry of Japan under the accession number of FERM-P No. 5636 (June 21, 1980) [now the accession number of FERM-BP No. 5 (May 1, 1981) (according to Budapest Treaty on the International Recognition of the Deposit of Microorganisms for the Purposes of Patent Procedure)] and in the American Type Culture Collection (ATCC) under ATCC number 31892 (May 9, 1981).

The SF-2103 strain easily varies in its properties, as is the case of other strains belonging to the genus Streptomyces. Such variations can be caused by irradiating, for example, with ultraviolet rays, X-rays, radioactive rays, and chemicals. Therefore, all such variants and mutants can be used in the process of the invention so long as they have the ability to produce the SF-2103A substance.

In accordance with the process of the invention, the above-described strain is cultivated in a medium containing nutrients which are assimilable by known microorganisms. Such nutrients can be known materials conventionally used in the cultivation of Actinomyces strains. Examples of carbon sources which can be used include glucose, glycerol, starch, dextrin, maltose syrup, molasses, and soybean oil. Examples of nitrogen sources which can be used include soybean meal, wheat germ, cottonseed meal, meat extract, peptone, yeast extract, corn steep liquor, ammonium sulfate, and sodium nitrate. Additionally, if desired, inorganic salts such as calcium carbonate, sodium chloride, magnesium sulfate, sodium sulfate, cobalt chloride, ferrous sulfate, and phosphates (particularly preferably, sodium sulfate and cobalt chloride), as well as those organic and inorganic materials which enhance microbial growth and the production of the desired SF-2103A substance can be added. Furthermore, if desired, a defoaming agent (for example, Silicon KM68-2F (produced by Shin-Etsu Chemical Industry Co., Ltd., Tokyo)) can be added.

For the cultivation of the Streptomyces sp. SF-2103, the liquid cultivation method, and particularly the submerged cultivation method under aerated conditions, is most suitable, as is often the case with the production of known antibiotics. The suitable temperature range for the cultivation is from 20° C. to 35° C. In many cases, it is preferred to effect the cultivation at the temperature range of from 23° C. to 30° C. The production of the SF-2103A substance reaches a maximum usually in 1 to 10 days in both shake-culture and tank-culture (submerged cultivation), although the optimum time varies depending on the medium and cultivation method being used.

The SF-2103A substance can be quantitatively determined by measuring the antibacterial activity thereof by a bioassay technique, using a suitable strain as a test organism as in the case of conventional antibiotics, because it is an antibacterial substance and has antibacterial activity against gram-positive and gram-negative bacteria. However, since the SF-2103A substance is characterized by having strong $\beta$-lactamase inhibitory activity as well as antibacterial activity, a newly devised $\beta$-lactamase inhibitory activity assay procedure as described hereinbelow can also be employed to determine it very quickly and accurately.

In accordance with the newly devised assay procedure, endo-$\beta$-lactamase produced by Proteus vulgaris M-8243 is employed as $\beta$-lactamase. The endo-$\beta$-lactamase is inoculated in a 2% Kyokuto bouillon solution (pH 7 before sterilization) and incubated at 32° C. Immediately after the start of the incubation, and 2 hours and 4 hours after the start of the incubation, a benzylpenicillin potassium salt was added as a $\beta$-lactamase induction substance so that the concentration thereof was 250 $\mu$g/ml, and the incubation was continued for 7 to 8 hours from the start thereof. At the end of that time, the incubation is stopped, and the strain is collected by centrifugal separation. The mass of wet cells thus obtained is suspended in a 0.1 M phosphate buffer solution (pH 7.0) whose volume is twice as much as the cells and is placed in a cell grinder (e.g., a French pressure cell) where cells are disrupted. The resulting suspension is subjected to centrifugal separation (10,000 rpm, 10 minutes) and cell fragments precipitated are removed. The thus obtained supernatant is dialyzed overnight with 0.1 M phosphate buffer solution (pH 7.0) at 5° C., and the dialyzate solution is obtained as a crude $\beta$-lactamase enzyme solution. The dialyzate solution has a $\beta$-lactamase activity of 5,000 to 6,000 units ($\mu$/ml) as determined by a modified method of the Sergeant's method of measuring enzyme activity described hereinafter.

The thus prepared $\beta$-lactamase is used to prepare an assay plate. A 2.3% solution of Nutrient Agar (produced by Difco Corp.) is sterilized in an autoclave and is cooled to 45° C. To 250 ml of the solution are added 0.5 ml of a seed of Bacillus subtilis ATCC 6633 which has been previously cultivated for seed, and a 125 unit amount of the foregoing $\beta$-lactamase solution, which are then mixed. The resulting mixture is poured into a 250 mm $\times$ 320 mm plain plate and is solidified therein.

In performing the assay, 20 $\mu$l of a solution to be examined is placed on a paper disc (diameter, 8 mm) which has been provided with 20 $\mu$l of a 50% aqueous acetone solution of Cefalotin sodium salt at a concentration of 50 $\mu$g/ml, and it is then dried in air. The paper disc thus prepared is placed in an assay plate, and when it is maintained at 37° C. for 15 to 17 hours, the inhibitory zone appears to an extent depending on the concentration of the SF-2103A substance.

In this assay procedure, the logarithm of the concentration of the SF-2103A substance and the diameter of the inhibitory zone show a linear relation within the range of 0.03 $\mu$g/ml of 1 $\mu$g/ml of the concentration of the SF-2103A substance. Thus, the SF-2103A substance can be quantitatively determined accurately.

The SF-2103A substance is accumulated mainly in a culture broth filtrate. The SF-2103A substance contained in the culture broth can be extracted and purified according to the physical and chemical characteristics thereof as described hereinafter. For such extraction and purification, the following method is efficient.

A culture broth containing the desired substances is filtered to remove solid matter, and the resulting filtrate is adsorbed on active carbon and is then eluted with a 50% aqueous acetone solution. Fractions containing the desired substances are collected and concentrated. After distilling away the acetone, the desired substances are extracted with a haloalkane, e.g., dichloromethane, containing a quaternary ammonium salt such as benzyldimethylcetyl ammonium chloride or benzyldimethyltetradecyl ammonium chloride, and they are then re-extracted with water containing sodium iodide and freeze-dried to obtain a crude product of the SF-2103A substance.

For further purification of the crude SF-2103A substance, chromatography using anion exchange carriers, such as DEAE-Sephadex A-25, QAE-Sephadex A-25, DEAE-cellulose, and Dowex 1$\times$2, is repeated. Additionally, gel filter media, such as Biogel P-2, porous resins, such as Amberlite XAD, cellulose columns, etc., can be used to further purification for the crude SF-2103A substance.

Analysis of the thus-purified SF-2103A substance powder by thin layer chromatography using various solvents and other analytical methods (e.g., high voltage paper electrophoresis and high speed liquid chromatography) confirms that it is a single substance.

The SF-2103A substance is extremely unstable at temperatures higher than room temperature, or in an acidic or alkaline state as described hereinafter. In isolating the SF-2103A substance from the culture broth, care should be taken so that the solution does not become acidic or alkaline, and all operations should be performed quickly at low temperatures.

Furthermore, it is difficult to isolate the SF-2103A substance in a free acid form because it is, as described above, very unstable in an acidic state. The SF-2103A substance is therefore obtained as a salt thereof in a pale yellow or white amorphous powder form by freeze-drying a neutral aqueous solution thereof. The purity of the SF-2103A substance obtained varies depending on the potency of the culture broth.

The type of the salt is determined by the cation used in the purification. For example, when the purification is performed by chromatography using DEAE-Sephadex A-25 and with NaCl water as an eluate, the SF-2103A substance is obtained as a sodium salt thereof. Pharmaceutically acceptable salts other than the sodium salt include alkali metal (e.g., potassium) salts, alkaline earth metal (e.g., calcium) salts, inorganic salts (e.g., aluminum and ammonium salts), and organic salts (e.g., a substituted ammonium salt), which can be prepared in the same manner as used in the preparation of the sodium salt. Furthermore, the conversion of the sodium salt into another salt can be performed by passing an aqueous sodium salt solution through a cation exchange resin, such as Dowex 50W, which has been previously replaced with the cations desired to be exchanged.

Hereinafter, the physical and chemical properties of the sodium salt of the SF-2103A substance which is believed to the most pure product thus far obtained, are described. It is to be noted, however, that the SF-2103A substance sodium salt may contain water or other impurities because it is obtained as a freeze-dried powder.

The characteristics of the novel antibiotic SF-2103A substance and salts thereof are shown hereinbelow. The characteristics of the SF-2103A substance sodium salt are as follows:

(1) Color and Form: Obtained as a white powder by freeze-drying.

(2) Melting Point: No clear melting point. Discoloration to brown and decomposition forming bubbles occurs at 168° C.

(3) Specific Rotation: $[\alpha]_D^{20} -16.3$ (c 1, water)

(4) Elemental Analysis and Molecular Weight (Sample is vacuum-dried on phosphorus pentoxide at room temperature for 27 hours and then measured):

|   | Calculated for $C_9H_8NO_{10}S_2Na_3 \cdot 2H_2O$ (%) | Found (%) |
|---|---|---|
| C | 23.53 | 23.62 |
| H | 2.61 | 2.44 |
| N | 3.05 | 3.00 |
| O | 41.83 | 42.16 (balance) |
| S | 13.94 | 13.81 |
| Na | 15.03 | 14.97 (determined by atomic-absorption spectroscopy) |

The molecular weight is estimated to be about 450 judging from the elemental analytical values and nuclear magnetic resonance spectrum.

(5) Ultraviolet Absorption Spectrum: The ultraviolet absorption spectrum as determined in a 0.02 M phosphate buffer (pH 7.2) has maximum absorptions at 266 to 267 nm ($E_{1\,cm}^{1\%} = 126$) and 230 nm ($E_{1\,cm}^{1\%} = 118$) as shown in FIG. 1.

Figure 2:
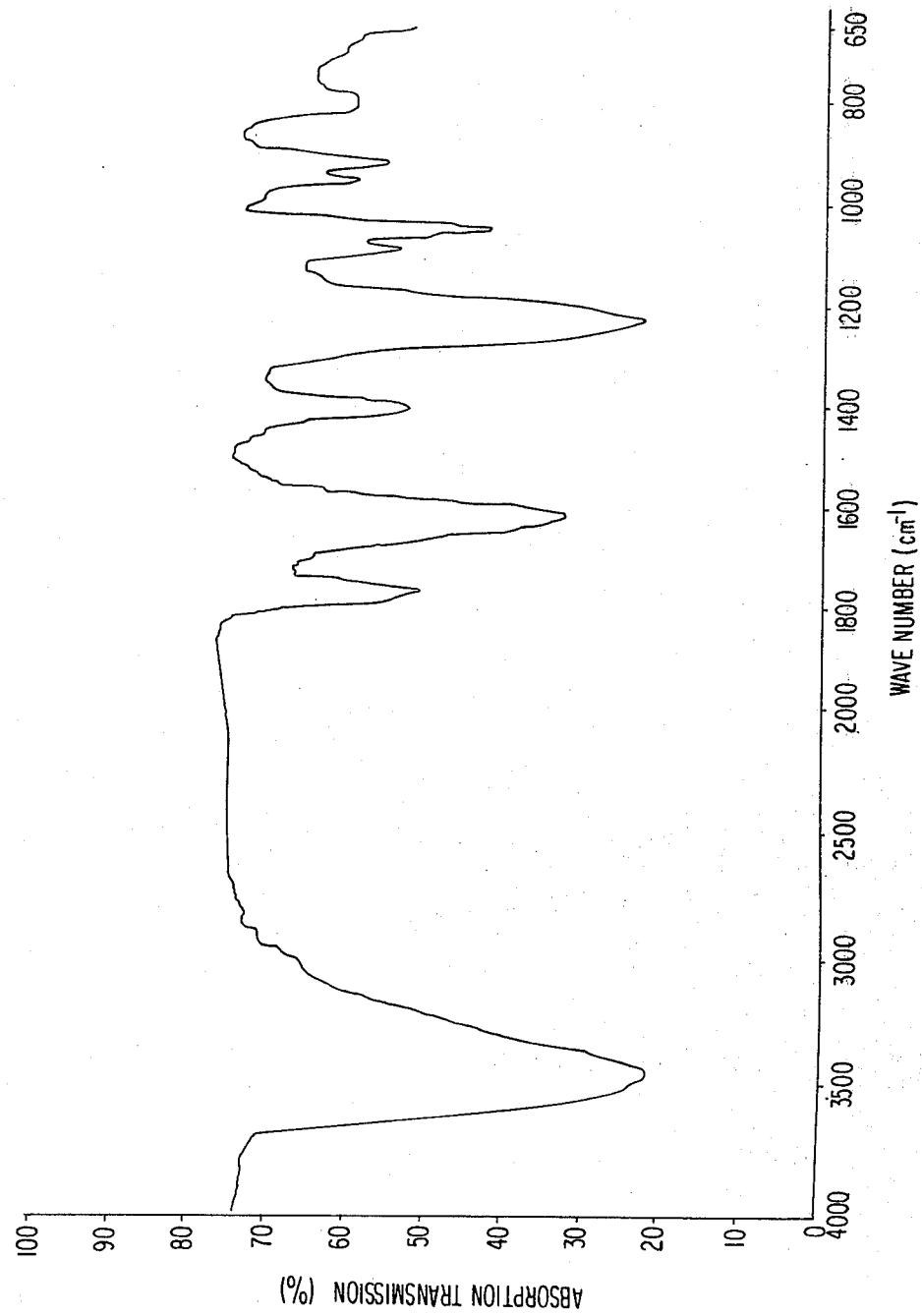

(6) Infrared Absorption Spectrum: The infrared absorption spectrum as determined by the potassium bromide tablet method is shown in FIG. 2 with absorption bands at 3450, 1755, 1610, 1390, 1220, 1080, 1040, 940, 900, 780 cm$^{-1}$.

Figure 3:
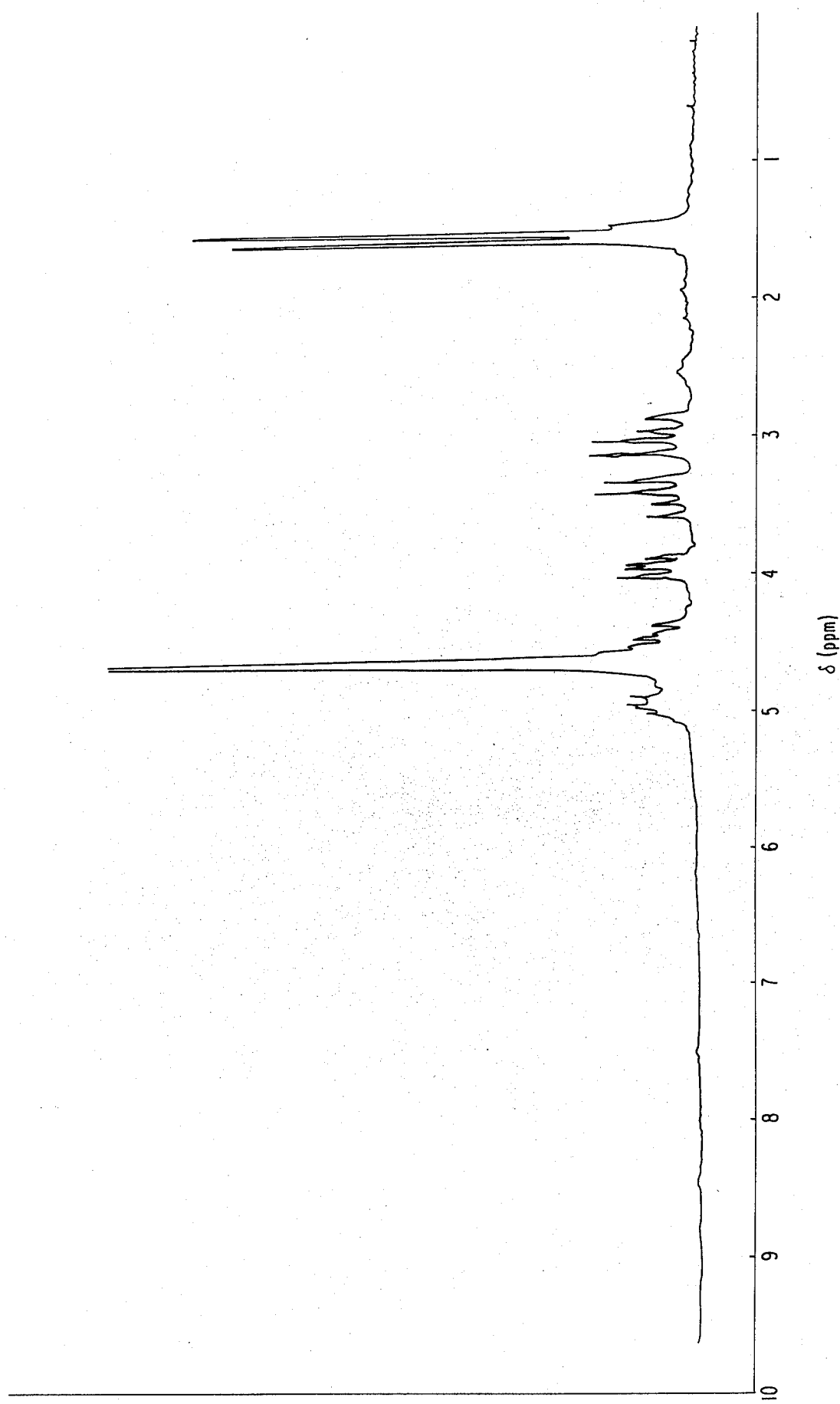

(7) Nuclear Magnetic Resonance Spectrum: The 100 MHz nuclear magnetic resonance spectrum as determined in heavy water with tetramethyl silane as an external standard is shown in FIG. 3 and has signals at $\delta 1.55$ (d, 3H), $\delta 2.99$ (dd, 1H), $\delta 3.44$ (dd, 1H), $\delta 3.94$ (dd, 1H), $\delta 4.48$ (m, 1H), and $\delta 4.94$ (m, 1H).

(8) Thin Layer Chromatography:

(a) Rf values as determined on a cellulose thin layer (Cellulose F$_{254}$, produced by Merck & Co.) with the solvent as shown below at 5° C. are as follows:

| Solvent | Rf Value |
|---|---|
| n-butanol/isopropanol/water (7/7/6 by volume) | 0.30 |
| 70% by vol. n-propanol aqueous solution | 0.52 |
| 70% by vol. ethanol aqueous solution | 0.62 |
| 80% by vol. acetonitrile | 0.37 |
| aqueous solution | |

(b) As determined on a DEAE-cellulose (Polygram CEL 300 DEAE, produced by Mercherry Nagel Corp.) with a 0.02 M phosphate buffer (pH 7.2) containing 0.1 M sodium chloride at 5° C., MC 696-SY2-A Substance as a control (the substance is described in *The Journal of Antibiotics,* Vol. 30, p. 770 (1970)) and is the same as MM 4550 Substance (described in *The Journal of Antibiotics,* Vol. B 32, p. 295 (1979)) shows an Rf value of 0.31, whereas the Rf value of the SF-2103A substance of the present invention is 0.14.

(9) High Voltage Paper Electrophoresis:

When electrophoresis is performed on a filter paper, Toyo Filter Paper No. 51 (produced by Toyo Roshi Co., Ltd.) having a width of 15 cm with the buffer described hereinbelow at a constant voltage of 2,800 volts for 15 minutes in a high voltage paper electrophoresis apparatus (produced by Servant Instrument Corp., high voltage electric source: HV 5000 A; electrophoresis tank: Model LT 48A), MC 696-SY2-A as a control (described in Japanese Patent Application (OPI) No. 14594/79 (the term "OPI" as used herein refers to a "published unexamined Japanese patent application")) moves to the anode side by 9.3 cm, whereas the SF-2103A substance of the present invention moves to the anode side by 15.3 cm. The buffer solution is prepared by adding water to 200 ml of pyridine and 8 ml of acetic acid so that the total volume is 3 liters, and the pH thereof is 6.4.

(10) High-Speed Liquid Chromatography:

As determined by high speed liquid chromatography under the conditions as described hereinbelow, the retention time of MC 696-SY2-A (as described hereinbefore) is 5 minutes and 40 seconds, whereas the SF-2103A substance of the present invention has a retention time of about 20 minutes.

Conditions: High-speed liquid chromatography

Apparatus ALC/GPC Model 244 (produced by Waters Corp.)

Column: ZIPAX SAX (produced by Du Pont Co., inner diameter: 7.9 mm, length: 50 cm)

Eluate: Prepared by dissolving sodium nitrate in a 0.05 M phosphate buffer (pH 7.2) at the concentration of 0.05 M.

Flow Rate: 3 ml/minute

Ultraviolet Absorption-Detecting Wavelength: 313 nm and 254 nm

Temperature: Room temperature (about 20° C.)

(11) Solubility: Freely soluble in water, soluble in methanol, and insoluble in ethyl acetate, chloroform and benzene.

(12) Color Reactions: Positive to Lemieux and Ehrlich reagents, and negative to Ninhydrin reagent.

On the basis of the physical and chemical properties as described above, it has been concluded that the substance (as the trisodium salt thereof) has the following structure:

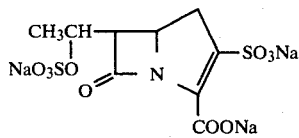

The SF-2103A substance exerts synergistic effects when used in combination with penicillin and cephalosporin antibiotic materials, which are ineffective to resistant bacteria producing β-lactamase, since it has β-lactamase inhibitory activity which is believed to be the principal characteristic of the SF-2103A substance, as well as antibacterial activity.

Hereinafter, several experimental results are shown to illustrate such activities of the SF-2103A substance.

The antibacterial activity of the SF-2103A substance sodium salt was determined by the agar dilution method in accordance with the standard method recommended by Japanese Chemotherapy Association (see *Chemotherapy*, Vol. 22, pp. 1126–1128 (1974)), and the results are shown in Table 2 below.

TABLE 2

| Test Organism | Minimum Inhibitory Concentration (μg/ml) |
| --- | --- |
| *Staphylococcus aureus* 209P | 25 |
| *Staphylococcus aureus* Smith | 25 |
| *Bacillus subtilis* ATCC 6633 | 50 |
| *Escherichia coli* No. 29 | 3.13 |
| *Escherichia coli* NIHJ JC-2 | 12.5 |
| *Klebsiella pneumoniae* PCI 602 | 50 |
| *Proteus mirabilis* GN 310 | 50 |
| *Proteus vulgaris* GN 76/C-1 | 25 |
| *Proteus morganii* Kono | 25 |
| *Shigella dysenteriae* Shigae | 3.13 |
| *Citrobacter freundii* GN 346 | 6.25 |
| *Serratia marcescens* No. 1 | 50 |
| *Pseudomonas aeruginosa* E-2 | >100 |

In this determination, Heart Infusion Agar (produced by Eiken Chemical Co., Ltd.) was used as the medium.

The determination of β-lactamase inhibitory activity of SF-2103A substance by the Sargent's method (see M. G. Sargent, *Journal of Bacteriology*, Vol. 95, p. 1493 (1968)) has revealed that it has strong β-lactamase inhibitory activity.

Assay of β-lactamase activity by the Sargent's method

The Sargent's method was partly modified as follows

Reagents

Reagent A: Enzyme solution properly diluted with 0.1 M phosphate buffer (pH 7.0) as to show 0.6 optical density of consumption of iodine at 490 nm when measured under the undermentioned conditions.

Reagent B: 1.3% Penicillin G potassium salt aqueous solution for penicillinase assay. 1.3% Cefalotin sodium salt aqueous solution for cephalosporinase assay (β-lactamase of *Proteus vulgaris* M-8243 or *Citrobacter freundii* GN 346).

Reagent C: 0.1 M phosphate buffer (pH 7.0)

Reagent D: Iodine acetate buffer solution which is prepared by adding 5 ml of stock iodine solution* to 95 ml of pH 4.0 acetate buffer (80 g of anhydrous sodium acetate adjusted to pH 4.0 with acetic acid and made up to 2 liters with distilled water).

*Stock iodine solution contains 0.32 N iodine and 1.2 M potassium iodide, prepared by dissolving 20.3 g of iodine and 100 g of KI in 500 ml of distilled water.

Assay Procedure

A reaction mixture consisted of 0.5 ml of Reagent B and 2 ml of Reagent C is pre-incubated for 5 min at 30° C., and 0.5 ml of Reagent A is added to it and kept for 30 min at 30° C. At the end of reaction, 5 ml of Reagent D is added with rapid mixing and kept for 10 min at 30° C., then the optical density at 490 nm is measured.

As the blank test, an incubation mixture containing 0.5 ml of Reagent B and 2 ml of Reagent C is kept at 30° C. for 30 min, after that 5 ml of Reagent D and 0.5 ml of Reagent A are added to it. Then the optical density is measured in the same way.

Assay of β-lactamase inhibitory activity

The determination of β-lactamase inhibitory activity is performed in the same manner as for the determination of β-lactamase activity as described above, except that a solution prepared by diluting an inhibitory substance with the Reagent C as described above is employed as Reagent C.

The blank test is procedured in the same way as the case of the assay of β-lactamase activity using Reagent C containing the inhibitor. Thus, the concentration of the SF-2103A substance required to cause 50% inhibition of Penicillinase was determined.

In order to examine the inhibitory activity of the antibiotic SF-2103A substance against other β-lactamase, i.e., an enzyme produced by *Proteus vulgaris* M-8243 and an enzyme produced by *Citrobacter freundii* GN 346 (both were prepared by the above-described preparation method), the same procedure as for Penicillinase was performed, with the exception that the foregoing β-lactamases were used in place of Penicillinase in Reagent A, and a Cefalotin sodium salt was used in place of the Penicillin G potassium salt in Solution B. The results are shown in Table 3.

One unit of β-lactamase activity according to Sargent's method as used herein is defined as the amount of enzyme necessary to decompose 1 μmol of a Penicillin G potassium salt or Cefalotin sodium salt per 60 minutes under the conditions for the present determination method.

TABLE 3

β-Lactamase Inhibitory Activity of SF-2103A Substance

| β-Lactamase | Substrate | Inhibitory Ratio |
| --- | --- | --- |
| Penicillinase | Penicilline G Potassium Salt | 34.4% at 10 g/ml |
| *Proteus vulgaris* M-8243 | Cefalotin Sodium Salt | 50% Inhibitory Concentration ($I_{50}$): 0.013 μg/ml |
| *Citrobacter freundii* GN 346 | Cefalotin Sodium Salt | 50% Inhibitory Concentration ($I_{50}$): 0.18 μg/ml |

The effect of the SF-2103A substance as a β-lactamase inhibitory agent against β-lactamase-producing bacterial strains was examined with respect to Ampicillin, Carbenicillin, Cefalotin, Cefaloridine. As β-lactamase-producing strains, *Proteus vulgaris* M-8243 (producing a wide range of Cephalosporinase), *Proteus rettgeri* GN 624 (producing typical Cephalosporinase), and *Citrobacter freundii* GN 346 (producing typical Cephalosporinase) were employed. Assay agar plates inoculated with these strains were prepared by a conventional procedure. Each of 10 μg of Ampicillin, 2 μg of Carbenicillin, 2 μg of Cefalotin, and 5 μg of Cefaloridine was placed on a paper disk of a diameter of 8 mm and, furthermore, the SF-2103A substance was added in an amount of 1 μg, 0.2 μg and 0.04 μg, as indicated in Table 4.

These paper disks were placed on the agar plates of the β-lactamase-producing strains, and the incubation was performed at 37° C. for 16 hours to examine the presence of the inhibition zone. The results are shown in Table 4.

TABLE 4

Synergistic Effects of SF-2103A Substance in Combination with β-Lactam Antibiotics

| Antibiotics | | Diameter of Inhibition Zone (mm) | | |
|---|---|---|---|---|
| | | Proteus vulgaris M-8243 | Proteus rettgeri GN 624 | Citrobacter freundii GN 346 |
| Ampicillin (10 μg) | | 0 | 0 | 0 |
| Ampicillin (10 μg) | + SF-2103A (1 μg) | 20.9 | 14.6 | 19.7 |
| Ampicillin (10 μg) | + SF-2103A (0.2 μg) | 20.0 | 10.0 | 11.3 |
| Ampicillin (10 μg) | + SF-2103A (0.04 μg) | 18.0 | 0 | 0 |
| Carbenicillin (2 μg) | | 0 | 0 | 0 |
| Carbenicillin (2 μg) | + SF-2103A (1 μg) | 15.2 | 16.7 | 13.6 |
| Carbenicillin (2 μg) | + SF-2103A (0.2 μg) | 13.3 | 11.1 | 11.7 |
| Carbenicillin (2 μg) | + SF-2103A (0.04 μg) | 12.1 | 0 | 10.0 |
| Cefalotin (2 μg) | | 0 | 0 | 0 |
| Cefalotin (2 μg) | + SF-2103A (1 μg) | 15.3 | 11.5 | 16.6 |
| Cefalotin (2 μg) | + SF-2103A (0.2 μg) | 14.8 | 0 | 11.0 |
| Cefalotin (2 μg) | + SF-2103A (0.04 μg) | 14.1 | 0 | 9.0 |
| Cefaloridine (5 μg) | | 0 | 0 | 0 |
| Cefaloridine (5 μg) | + SF-2103A (1 μg) | 16.2 | 14.3 | 17.3 |
| Cefaloridine (5 μg) | + SF-2103A (0.2 μg) | 16.2 | 9.0 | 12.0 |
| Cefaloridine (5 μg) | + SF-2103A (0.04 μg) | 14.2 | 0 | 0 |
| SF-2103A (1 μg) | | 0 | 0 | 0 |

For the paper disks containing no SF-2103A substance, the inhibition zone was not observed, whereas for the paper disks containing the SF-2103A substance in combination with the β-lactam antibiotics, the inhibition zone was observed, varying depending on the concentration of the SF-2103A substance. This indicates that the SF-2103A substance inhibits β-lactamase produced by the test organism, and as a result, the β-lactam antibiotic can exhibit the antibacterial activity thereof. The SF-2103A substance when used alone does not show the inhibition zone for the test organisms even in the maximum concentration (1 μg).

It is therefore clear that the SF-2103A substance has antibacterial activity and at the same time, exerts syngeristic effects in combination with the β-lactam antibiotics.

The antibacterial activity of the SF-2103A substance was examined by mouse protection test using mice, as described hereinafter, and it has been found that the SF-2103A substance is an antibiotic exhibiting sufficient effectiveness for practical use as an infection curing agent when used either alone or in combination with each of other proper antimicrobial agents (e.g., β-lactam antibiotics).

Four-week old male mice of the ICR-JCL strain (average weight: 20.6 g) were used in groups of five each.

Escherichia coli GN206 or Proteus vulgaris GN76/C-1 was inoculated on a plate of Heart Infusion Agar (produced by Eiken Chemicals Co., Ltd.) and cultured at 37° C. for 20 hours. The cells thus formed were collected and suspended in a physiological saline solution to prepare a cell suspension containing therein a predetermined number of cells. Equal volumes of the cell suspension and a 5% mucin solution (produced by Nakarai Chemicals Co., Ltd.) were mixed to prepare a cell solution having a cell concentration of $7.1 \times 10^7$ CFU/ml (CFU=colony forming unit).

Then, 0.5 ml of the cell solution as prepared above was intraperitoneally infected into the mice. Once after 1 hour, or twice at one and two hours after the infection, the test antibiotic was subcutaneously administered. Thereafter, the mice were observed for 7 days.

EXPERIMENT I

Escherichia coli GN206 was used as an infectious becterium, and a dose of 2 mg/mouse of the SF-2103A substance dissolved in a 1/75 M phosphate buffer (pH 7.0, containing 0.85% of sodium chloride) was administered once at one hour after the infection of the bacteria, and a dose of 1 mg/mouse of the SF-2103A substance was administered twice at one and two hours after the infection. In the former case, two of the five mice survived, and four of the five mice survived in the latter case. On the other hand, in the case of Control group wherein only 0.2 ml of the phosphate buffer was administered in the same manner as above, no survival was observed.

EXPERIMENT II

Proteus vulgaris GN-76/C-1 was used as an infectious bacterium, and a 1:1 mixed drug of the SF-2103A substance and Cefalotin (produced by Shionogi & Co., Ltd.) was administered. The mixed drug was administered twice (at one and two hours after the infection of the bacteria) each in a dose of 0.5 mg/mous, or twice (at one end two hours after the infection) each in a dose of 1 mg/mouse. In the former case, three of the five mice survived, and in the latter case, all of the five mice survived. On the other hand, in the case of Control group wherein only the phosphate buffer was administered, no survival was observed.

The toxicity of the SF-2103A substance sodium salt was measured by oral administration, intramuscular injection or intravenous injection in mice or rat. $LD_{50}$ values by oral administration, intramuscular injection and intravenous injection were all higher than 2,000 mg/kg.

The SF-2103A substance is valuable antibiotic which not only exhibits antimicrobial activities against various gram-positive and gram-negative bacteria, but also is effective against those resistant bacteria producing β-lactamases. Therefore, it can be used as a drug for human beings and domestic animals, and furthermore, as a sterilizing agent for the storage of food and medical instruments or devices.

The SF-2103A substance and salts thereof may be administered orally, topically or parenterally in the form of a preparation, for example, tablets, capsules, creams, syrups, suspensions, liquid preparations, powders, or injections and injections which are suitable for sterilization.

Although the SF-2103A substance can be used alone, it is effective when used in combination with other antibiotics, particularly β-lactam antibiotics, because it exerts synergistic effects therewith.

When the SF-2103A substance or salts thereof is used in combination with β-lactam antibiotics, the weight ratio of the SF-2103A substance or salts thereof to the β-lactam antibiotics may range about 20:1 to about 1:12, preferably 10:1 to 1:10, and particularly preferably 3:1 to 1:3.

The SF-2103A substance or salt thereof can be administered at a dose of 50 to 6,000 mg, generally 500 to 3,000 mg, per day.

By comparing the physical and chemical properties and biochemical characteristics as described above with those of known antibiotics, it can be seen that the SF-2103A substance is a novel antibiotic.

The following examples are given to illustrate the invention in greater detail. The % values in the examples are weight % values, unless otherwise indicated.

EXAMPLE 1

A liquid medium containing 1% of glucose, 1% of starch, 2% of soybean powder, 0.5% of cottonseed cake, 0.2% of sodium sulfate, 0.2% of calcium carbonate, and 0.0001% of cobalt chloride was adjusted to pH 7. Then, 80 ml portions of the liquid medium were separately introduced into a hundred 500-ml Erlenmeyer flasks, which were each plugged with a cotton pad and sterilized under pressure at 120° C. for 10 minutes. The SF-2103A substance (FERM-P No. 5636) was fully grown in a precultivation medium containing 1% of glucose, 1% of starch, 0.2% of soybean powder, 0.5% of peptone, 0.3% of yeast extract, 0.2% of meat extract and 0.2% of calcium carbonate to prepare a seed culture. Then, 1.5% portions of the seed culture thus-prepared were each inoculated in the liquid medium and incubated on a shaker at 28° C. for 3 days to obtain 7 l of a medium containing 3.5 µg/ml of the SF-2103A substance.

EXAMPLE 2

A liquid medium containing 1% of glucose, 1% of soluble starch, 0.2% of soybean powder, 0.5% of peptone, 0.3% of yeast extract, 0.2% of meat extract, and 0.2% of calcium carbonate was prepared and adjusted to pH 7.0. Then, 80 ml portions of the liquid medium were separately introduced into three 500-ml Erlenmeyer flasks, which were each plugged with a cotton pad and sterilized in an autoclave at 120° C. for 15 minutes. One platinum loopful of the SF-2103A substance (FERM-P No. 5636) was inoculated in each liquid medium and incubated on a shaker at 28° C. for 2 days to prepare a seed culture. Thereafter, 600 ml portions of the same medium above were separately introduced into three 5-l Erlenmeyer flasks, which were each plugged with a cotton pad and sterilized in an autoclave. The each seed culture prepared in one 500-ml flask above was inoculated in each one 5-l flask. After incubation on a shaker at 28° C. for 2 days, sufficient growth was observed.

Then, 200 l of a culture medium containing 2.0% of starch syrup, 1.2% of soybean powder, 1.2% of wheat germ, 0.3% of soybean oil, 0.02% of sodium sulfate, 0.0005% of ferrous sulfate, 0.00005% of cobalt chloride, and 0.1% of calcium carbonate was prepared in a 300-l fermentation tank (produced by Marubishi Co., Ltd.) (pH before sterilization: 7.0), and was sterilized under pressure at 120° C. for 30 minutes. After cooling of the culture medium, the culture prepared above (all of three 5-l Erlenmeyer flasks) was inoculated in the culture medium and the cultivation was performed while aerating and stirring at 28° C. The rate of rotation was 100 rpm (revolutions per minute) at the beginning and was increased to 150 rpm after 40 hours. The amount of aeration was 200 l/minute throughout the total cultivation period. After 68 hours, the cultivation was stopped, and the culture obtained contained 4.1 µg/ml of the SF-2103A substance.

EXAMPLE 3

(i) The same procedure as in Example 2 was repeated using three 300-l fermentation tanks to obtain 450 l of a culture filtrate of the SF-2103A substance (FERM-P No. 5636). The average unit of the SF-2103A substance was 2.1 µg/ml.

(ii) The SF-2103A substance was isolated as follows:

After adjustment of 425 l of the culture filtrate as obtained above to pH 5.0 with 6 N hydrochloric acid, 12.7 kg of active carbon (produced by Wako Pure Chemical Industries Ltd.) was added and stirred for 30 minutes in a stirring tank to allow adsorption thereonto of the effective ingredients. The active carbon was filtered off, and after washing with 50 l of water, 100 l of 50% aqueous acetone was added. The resulting mixture was adjusted to pH 8.0 with a 5 N sodium hydroxide solution and stirred for 30 minutes to elute the effective ingredients. After separation and removal of the active carbon, 100 l of the solution thus-eluted was concentrated to 45 l by distilling away the acetone. Then, 30 l of dichloromethane containing 0.2% (w/v) of benzyldimethylcetyl ammonium chloride was added to the above concentrated solution and stirred to extract the effective ingredients. To the extract thus obtained was added 4 l of an aqueous solution containing 1% (w/v) of sodium iodide to transfer the effective ingredients into an aqueous layer. The aqueous layer was passed through a column packed with 1.5 l of DEAE-Sephadex A-25 (produced by Pharmacia Co.) which had been buffered with a phosphate buffer with a pH of 7.4 to allow adsorption thereonto of the effective ingredients. After preliminary washing with 15 l of 0.1 M NaCl aqueous solution dissolved in a 20 mM phosphate buffer (pH 7.4), the effective ingredients were eluted with 0.2 M NaCl aqueous solution dissolved in the same buffer as used above. The eluate was divided into 100 ml fractions, and Fractions 108 to 132 were obtained as active fractions. Then, 24 l of the active fractions was passed through a column packed with 240 ml of active carbon to allow the active carbon to adsorb thereon the effective ingredients. After washing the column with 400 ml of water, the effective ingredients were eluted with 1 l of a 50% aqueous acetone solution. The eluate was concentrated under reduced pressure. On freeze-drying the concentrated liquid, 709 mg of a powder of a crude SF-2103A substance (purity: about 24%) was obtained.

(iii) The same procedure as in (i) above was repeated, using two 300-l fermentation tanks to obtain 285 l (2.6 µg/ml) of a culture filtrate. The culture filtrate was adjusted to pH 6.2 with 6 N hydrochloric acid. To the filtrate was added 95 l of dichloromethane containing 0.2% (w/v) of benzyldimethyltetradecyl ammonium chloride, and the resulting mixture was stirred for 1 hour to extract the effective ingredients. To the extract thus obtained was added 8.5 l of a 0.7% (w/v) aqueous sodium iodide solution, and the resulting mixture was stirred for 20 minutes to transfer the effective ingredients into an aqueous layer. The aqueous layer was concentrated under reduced pressure by distilling away the dichloromethane. The thus-concentrated liquid was passed through a column packed with 400 ml of active carbon (produced by Wako Pure Chemical Industries Ltd.) which had been charged with water, and then the active carbon was washed with 300 ml of water. The liquid and washing water passed through the active carbon were combined, and 8.3 l of the combined liquid was passed through a column packed with 1 l of DEAE-Sephadex A-25 (produced by Pharmacia Co.) which had been buffered with a phosphate buffer having a pH of 7.4 to allow to adsorb thereon the effective ingredients. After preliminary washing with 10 l of 0.2 M NaCl aqueous solution dissolved in a 20 mM phosphate buffer (pH 7.4), the effective ingredients were eluted with 0.3 M NaCl aqueous solution dissolved in the same buffer as used above. The eluate was divided into 150 ml fractions, and Fractions 17 to 53 were confirmed to be active. These active fractions were combined, and 5.5 l of the combined active fractions was passed through a column packed with 1.2 l of active carbon (produced by Wako Pure Chemical Industries Ltd.), which had been charged with water, to allow to adsorb thereon the effective ingredients. After washing the column with 2.3 l of water, the effective ingredients were eluted with 5.5 l of 50% aqueous acetone. The eluate thus obtained was concentrated under reduced pressure. On freeze-drying the concentrated liquid, 540 mg of a powder of a crude SF-2103A substance (purity: about 40%) was obtained.

(iv) The powder of the crude SF-2103A substance obtained in (iii) above in the amount of 540 mg was dissolved in 40 ml of water. The resulting solution was passed through a column packed with 100 ml of DEAE-Sephadex A-25 which had been buffered with a phosphate buffer having a pH of 7.2 to allow to adsorb thereon the effective ingredients. After washing with 200 ml of a 20 mM phosphate buffer (pH 7.2), the effective ingredients were eluted with 0.2 M NaCl aqueous solution dissolved in the same buffer as used above.

The eluate was divided into 20 ml fractions, and Fractions 110 to 165 were confirmed to be active. These active fractions were combined and passed through a column packed with 175 ml of active carbon to allow to adsorb thereon the effective ingredients. After washing of the active carbon with 300 ml of water, the effective ingredients were eluted with 800 ml of 50% aqueous acetone.

When the eluate was concentrated under reduced pressure and freeze-dried, the sodium salt of the SF-2103A substance was obtained in the amount of 206 mg (purity: about 64%) as a pale yellow powder.

Then, 200 mg of the powder was dissolved in 2 ml of water, and the resulting solution was passed through a column packed with 250 ml of Diaion HP-20AG (produced by Mitsubishi Chemical Industries Ltd.). After development with water, the eluate was divided into 7 ml fractions, and Fractions 18 to 26 were confirmed to contain the effective ingredients. Of these active fractions, Fractions 22 to 24 were chosen and combined, concentrated under reduced pressure, and freeze-dried, and thus 60 mg of the sodium salt of the SF-2103A substance (purity: about 77%) was obtained as a slightly yellow powder.

(v) In 1 ml of water was dissolved 60 mg of the slightly yellow powder obtained in (iv) above. The resulting solution was passed through a column packed with 200 ml of Sephadex G-10 (produced by Pharmacia Co.) and developed with water. The eluate was divided into 7 ml fractions, and Fractions 11 to 16 were confirmed to be active. Fractions 12 and 13 were combined, concentrated under reduced pressure, and freeze-dried, and thus 32 mg of a sodium salt of a pure SF-2103A substance was obtained as a white powder.

The foregoing operations (ii) to (v) were performed under a low temperature condition (about 4° C.).

While the invention has been described in detail and with reference to specific embodiments thereof, it will be apparent to one skilled in the art that various changes and modifications can be made therein without departing from the spirit and scope thereof.

What is claimed is:

1. An antibiotic SF-2103A substance or non-toxic salt thereof, wherein the trisodium salt thereof has the following properties:
   (1) Color and Appearance: Obtained as a white powder by freeze-drying;
   (2) Melting Point: Shows no distinct melting point, and turns brown and decomposes forming bubbles at 168° C.;
   (3) Specific Rotation: $[\alpha]_D^{20} - 16.3°$ (c 1, water);
   (4) Elemental Analysis: Calculated for $C_9H_8NO_{10}S_2\cdot Na_3\cdot 2H_2O$

|  | Calculated (%) | Found (%) |
|---|---|---|
| C | 23.53 | 23.62 |
| H | 2.61 | 2.44 |
| N | 3.05 | 3.00 |
| O | 41.83 | 42.16 (balance) |
| S | 13.94 | 13.81 |
| Na | 15.03 | 14.97 (as determined by atomic absorption analysis) |

(5) Ultraviolet Absorption Spectrum: As shown in FIG. 1, the maximum absorptions in a 0.02 M phosphate buffer (pH 7.2) are present at 266 to 267 nm ($E_{1\ cm}^{1\%} = 126$) and 230 nm ($E_{1\ cm}^{1\%} = 118$);
   (6) Infrared Absorption Spectrum: The infrared absorption spectrum as determined by the potassium bromide tablet method is shown in FIG. 2 with absorption bands at 3450, 1755, 1610, 1390, 1220, 1080, 1040, 940, 900, 780 cm$^{-1}$;
   (7) Nuclear Magnetic Resonance Spectrum: The 100 MHz nuclear magnetic resonance spectrum as determined in heavy water with tetramethylsilane as an external standard is shown in FIG. 3 and has signals at $\delta 1.55$ (d, 3H), $\delta 2.99$ (dd, 1H), $\delta 3.44$ (dd, 1H), $\delta 3.94$ (dd, 1H), $\delta 4.48$ (m, 1H), and $\delta 4.94$ (m, 1H);
   (8) Thin Layer Chromatography:
   (a) Rf values on a cellulose thin layer (Cellulose F$_{254}$, produced by Merck & Co.) as developed at 5° C. with the following solvents:

| Solvent | Rf |
| --- | --- |
| n-butanol/isopropanol/water (7/7/6 by volume) | 0.30 |
| 70% by vol. n-propanol aqueous solution | 0.52 |
| 70% by vol. ethanol aqueous solution | 0.62 |
| 80% by vol. acetonitrile aqueous solution | 0.37 |

(b) When developed on DEAE-cellulose (Polygram CEL 300 DEAE, produced by Mercherry Nagel Corp.) at 5° C. with a 0.02 M phosphate buffer (pH 7.2) containing 0.1 M sodium chloride, MC 696-SY2-A Substance as a control shows an Rf value of 0.31, whereas the SF-2103A substance shows an Rf value of 0.14;

(9) Solubility: Freely soluble in water, soluble in methanol; insoluble in ethyl acetate, chloroform, and benzene; and

(10) Color Reactions: Positive for the Lemieux and Ehrlich reagents, and negative for the Ninhydrin reagent.

2. An antibiotic SF-2103A substance having the formula

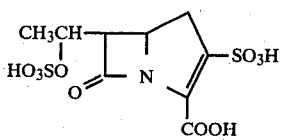

or a non-toxic salt thereof.

3. An antibiotic composition comprising an antibiotic SF-2103A substance or a non-toxic salt thereof as in claim 1 or 2.

* * * * *